United States Patent [19]
Andreiko et al.

[11] Patent Number: 5,542,842
[45] Date of Patent: Aug. 6, 1996

[54] BRACKET PLACEMENT JIG ASSEMBLY AND METHOD OF PLACING ORTHODONTIC BRACKETS ON TEETH THEREWITH

[75] Inventors: Craig A. Andreiko, Alta Loma; Mark A. Payne, Whittier, both of Calif.

[73] Assignee: Ormco Corporation, Glendora, Calif.

[21] Appl. No.: 462,657

[22] Filed: Jun. 5, 1995

Related U.S. Application Data

[63] Continuation-in-part of Ser. No. 973,965, Nov. 9, 1992.

[51] Int. Cl.$^6$ ................................................ A61C 3/00
[52] U.S. Cl. ................................................ 433/3; 433/8
[58] Field of Search .................................. 433/3, 8, 9, 24

[56] References Cited

U.S. PATENT DOCUMENTS

| | | | |
|---|---|---|---|
| 3,686,762 | 8/1972 | Sutter. | |
| 3,738,005 | 6/1973 | Cohen et al. | 433/3 |
| 3,871,098 | 3/1975 | Dean | 433/3 |
| 4,183,141 | 1/1980 | Dellinger et al. | |
| 4,284,405 | 8/1981 | Dellinger | 433/24 |
| 4,360,341 | 11/1982 | Dellinger | 433/24 |
| 4,424,029 | 1/1984 | Maijer et al. | 433/3 |
| 4,626,208 | 12/1986 | Hall | 433/3 |
| 4,850,864 | 7/1989 | Diamond | 433/3 |
| 5,055,038 | 10/1991 | Ronay et al. | 433/24 |
| 5,062,793 | 11/1991 | Cleary et al. | 433/3 |

FOREIGN PATENT DOCUMENTS

WO9410935  5/1994  WIPO.

*Primary Examiner*—Nicholas D. Lucchesi
*Attorney, Agent, or Firm*—Wood, Herron & Evans, P.L.L.

[57] ABSTRACT

A method and apparatus for accurately positioning and orienting an orthodontic appliance relative to individual teeth of a patient is provided, preferably in the form of a pivot action jig, preferably of two parts pivotally linked together. Preferably, one part releasably engages an orthodontic bracket relative to a pivot axis at which the two parts are connected, preferably by fitting between spaced vertical tie wings of the bracket with a blade fitting in a bracket slot. The second jig part [includes a tooth-engaging surface configured to the shape of the crown of the tooth. Where the bracket itself is configured to pivotally attach to the jig, the jig may be formed of only the tooth engaging part. Preferably, the tooth-engaging surface uniquely fits over the occlusal end of the crown and includes a slight over center end, opposite the pivot connection, and may include a three-dimensional cap. A bracket is positioned in the jig, the assembly of the jig and the bracket is brought against the labial or lingual side of the crown of the tooth, and the tooth engaging part of the jig is pivoted to move the tooth-engaging surface gingivally into a unique position and orientation against the crown. This uniquely positions the bracket in a position where it is bonded to the tooth. When the bond has hardened, the tooth engaging part is pivoted occlusally away from the tooth and the jig is disconnected from the bracket.

14 Claims, 2 Drawing Sheets

BRACKET PLACEMENT JIG ASSEMBLY AND METHOD OF PLACING ORTHODONTIC BRACKETS ON TEETH THEREWITH

This application is a continuation-in-part of U.S. patent application Ser. No. 07/973,965, filed Nov. 9, 1992, entitled Custom Orthodontic Bracket and Bracket Forming Method and Apparatus, which is related to Ser. No. 07/973,844, filed Nov. 9, 1992, entitled Method and Apparatus for Forming Jigs for custom Placement of Orthodontic Appliances on Teeth and Jigs Formed Therewith, now U.S. Pat. No. 5,368,478, which are continuations-in-part of:

U.S. application Ser. No. 07/775,589, filed Oct. 15, 1991, entitled Method of Forming Orthodontic Brace, now abandon, of which U.S. application 08/141,376, filed Oct. 22, 199, and now U.S. Pat. No. 5,395,238, is a continuation in part; and of:

U.S. patent application Ser. No. 08/222,315, filed Apr. 1, 1994, which is a continuation of U.S. patent application Ser. No. 07/875,663, filed 29 Apr. 1992, entitled Method of Forming Orthodontic Brace, now abandon, which is a continuation of U.S. patent application Ser. No. 07/467,162, filed Jan. 19, 1990, now abandon;

all of which are commonly owned by the assignee of the present application and all are hereby expressly incorporated into this application by reference.

FIELD OF THE INVENTION

The present invention relates to orthodontic appliances for straightening teeth. More particularly, the present invention relates to a method and apparatus for accurately locating orthodontic brackets on a patient's teeth.

BACKGROUND OF THE INVENTION

In the orthodontic treatment of patients, orthodontic appliances are secured to a patient's teeth. This most commonly involves the cementing of orthodontic archwire supporting brackets to crown surfaces of the patient's teeth. Standard orthodontic appliances are designed to fit average dental anatomies. An orthodontist using standard appliances selects, from the standard appliances available, appliances most suited for the particular patient's dental anatomy, to thereby minimize the amount of manual shaping of the appliance, such as bending the archwire, that the orthodontist must employ. In order to use the standard appliances to most effectively obtain the benefits of the appliance design in minimizing manual manipulation by the orthodontist, accurate placement of the appliance on the teeth at the precise positions contemplated in the appliance design is necessary. For this purpose, various gages and jigs have been proposed.

With the use of the custom orthodontic appliance such as those described in the related U.S. patent applications referred to above, it is possible that orthodontic finishing treatment proceed with almost no manual shaping of the appliance by the orthodontist. With such a custom appliance, however, the accurate placement of the appliance on the teeth is even more important than with the use of standardized appliances made to average geometries.

The provision of placement jigs for accurately securing orthodontic appliances to the teeth of a patient is most effective where the time and difficulty in using the jigs is kept to a minimum and where the likelihood of error in the use of the jig is similarly reduced. With the development of more refined designs of orthodontic appliances, and particularly with the use of custom designed orthodontic appliances, there is an increased need for error-free placement jigs that are easy for the orthodontist to use.

SUMMARY OF THE INVENTION

Accordingly, it is a primary objective of the present invention to provide an orthodontic appliance placement jig that can be used by an orthodontist to quickly and easily locate an orthodontic appliance, particularly the orthodontic brackets of the appliance, accurately on the teeth of a patient at precisely the intended positions.

It is a more particular objective of the present invention to secure orthodontic brackets on the teeth of a patient at precise locations on the crowns of the patients' teeth and with the archwire slots of the brackets precisely positioned and oriented to support an archwire according so as to satisfy the geometric parameters of the orthodontic appliance design.

According to the principles of the present invention, there is provided a jig having a tooth-engaging surface that conforms to the contour of the surface of the crown of a tooth onto which an appliance is to be connected, an appliance-engaging surface that engages the appliance in a predetermined orientation and position relative to the tooth shape conforming surface, and a linkage between the two engaging surfaces of the jig so as to allow the two surfaces to snap into and out of the predetermined relative orientation and position. More particularly, the appliance-engaging surface is configured to support a bracket such that the slot of the bracket is in the predetermined orientation.

In one embodiment of the invention, the tooth-engaging surface of the jig includes a two-dimensional contour that conforms to the profile of the occlusal end of the crown surface of the tooth in a vertical and labiallingually extending plane through the approximate center of the tooth so as to fit over the tooth to which a bracket is to be connected in one and only one position and orientation. In another and preferred embodiment of the invention, the tooth-engaging surface is a three-dimensional contour in the form of a partial cap that conforms to the occlusal end of the surface of the crown of the tooth. The three-dimensional contour may be molded from the tooth or a model or image thereof to form a three-dimensional cap, or it may be formed by N/C equipment, such as by cutting, by stereo lithography, or by otherwise machining or otherwise forming the contour into a three-dimensional block of material utilizing machine control commands programmed to replicate the shape of the tooth from a digital or mathematical model of the tooth or from data scanned from the tooth or physical model of the tooth.

Further, in the preferred embodiment of the invention, the jig is formed in two parts pivotally linked together. One part is the tooth-engaging part that carries the tooth-engaging surface positioned between a pivot connection with the other part and lever end by which the orthodontist can press the tooth-engaging surface onto the crown of the patient's tooth with a finger. The other part is the bracket-engaging part that carries the bracket-engaging surface having geometry for facilitating registration of bracket in a unique position and orientation in the jig. In one embodiment, the registration surface geometry includes a blade that fits into the archwire slot of the bracket and positions and orients the bracket to the jig. The bracket-engaging part preferably has an outer cylindrical surface opposite the bracket-engaging surface that functions as a pivot pin about which the tooth-engaging part, including the tooth-engaging surface and lever, pivots. Instead of a pivot pin, a resilient connection, or some other form of linkage can be used to achieve sufficient generally pivotal motion. Such pivot pin function can be provided by part of the permanent configuration of the bracket itself, such as by providing a cylindrical slotted bracket, or bracket in which the slot is formed in a horizontally oriented cylindrical support or post, having a mesio-distal axis, such that a jig may be formed of only one part that includes the tooth-engaging surface and lever portion, which pivotally clips onto and is removeable from, the post portion of the bracket.

Preferably, the tooth-engaging surface on the side of the tooth opposite the pivot connection diverges away from the pivot axis and then, at the farthest point from the pivot axis side of the tooth, curves very slightly toward the axis, so that the tooth-engaging surface will snap onto the tooth to a stable position. Preferably also, the tooth-engaging surface is so contoured to conform to the surface of the crown that it will fit sufficiently onto the tooth in only one unique position and orientation so that the jig will not snap onto the tooth unless the jig is positioned correctly on the tooth.

For use, a bracket is preferably preassembled to the jig. With a two part jig, the bracket is preferably connected to the jig of the preferred embodiment of the invention by fitting a blade of a pivot axis part of the jig into the archwire slot of the bracket. This positions and orients the bracket relative to a pivot axis defined by the cylindrical element in which the blade is supported. In other embodiments employing a cylindrical barrel or post in which the archwire slot is formed, the pivot axis for the jig is already a permanent part of the bracket. The lever portion of the jig is snap fit over the cylindrical pivot axis.

In use by the orthodontist, the bracket, with jig attached, is roughly positioned against a side of the tooth by moving the jig against the tooth with the pivot axis of the jig oriented generally in a horizontal mesial-distal direction. Then the lever portion of the jig is pivoted on the axis to move the tooth-engaging surface of the jig in a gingival direction to fit the tooth-engaging surface onto the occlusal extremity of the tooth. This motion forces the jig lever portion to assume a unique position and orientation relative to the tooth and accurately locates the pivot axis approximately parallel to the side of the tooth on which the bracket has been located, thereby forcing the bracket To a precise position and orientation on the tooth. Where the shape of the tooth permits, a slight over-center portion of the tooth-engaging surface of the jig on the side of the tooth opposite the bracket and the pivot axis causes the jig to fit with a stable snap action. The jig holds the bracket in position on the tooth until the adhesive is set to bond the bracket to the tooth. Then, the jig is pivoted to move the lever portion in the occlusive direction away form the tooth, and the bracket-engaging portion is disconnected from the bracket by withdrawing the blade from the bracket slot.

The jig of the present invention is useful for positioning standardized appliance brackets, but is most useful in accurately and precisely positioning custom brackets designed and manufactured to the specific anatomy of the individual patient. The jig has the advantage of providing the orthodontist with the capability of placing the bracket on the tooth and pressing it into its exact position in a matter of seconds by merely holding the jig, with the bracket-engaged thereto, between two fingers, or by using a small tool, and then directing the assembly into position by pressing the lever end against the tooth with a tool or finger. The positioning of the jig and bracket on the tooth can be carried out without visually locating or orienting the assembly or otherwise visually monitoring the positioning. The placement can be carried out by touch and reliance on the tendency of the jig to seek the position on the tooth that is uniquely designed to fit. The jig can be used for attaching brackets on either the labial or lingual sides of the teeth.

These and other objectives and advantages of the present invention will be more readily apparent from the following detailed description of the drawings and preferred embodiments, in which:

DETAILED DESCRIPTION OF THE PREFERRED EMBODIMENTS

Figure 1:
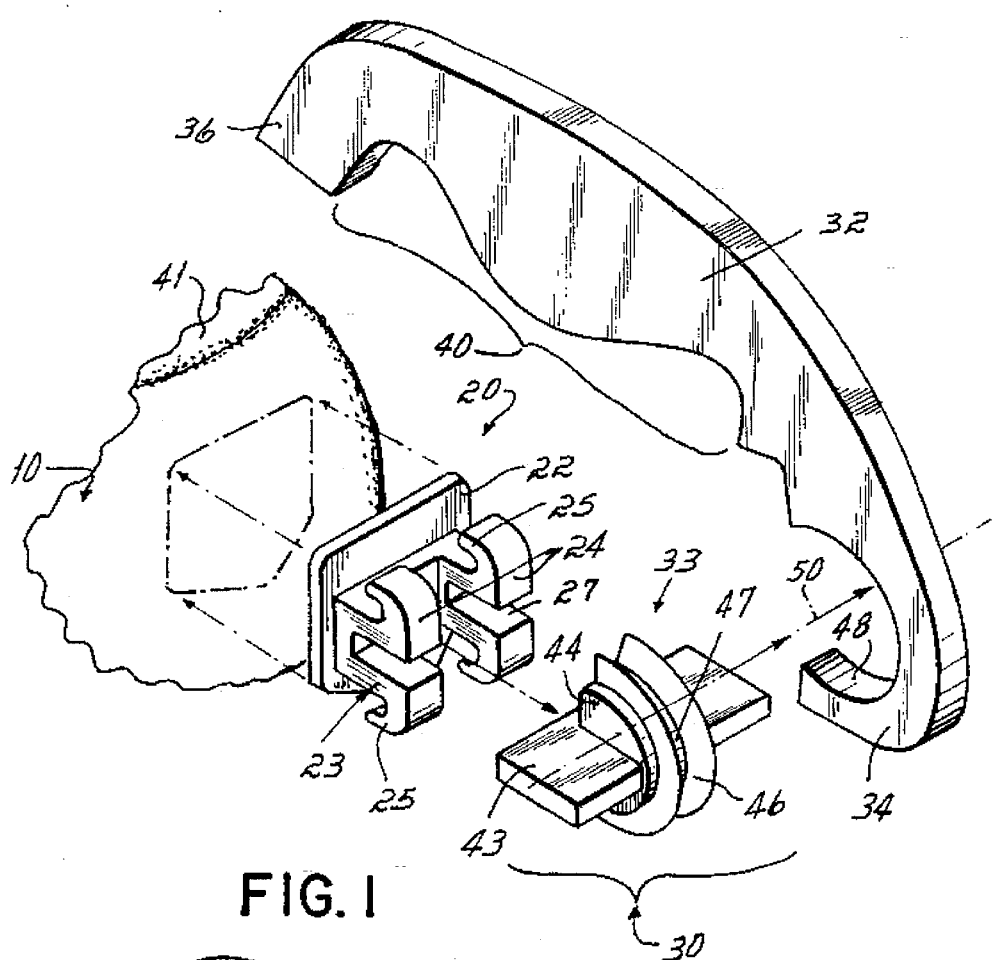
FIG. 1 is a disassembled isometric view of one preferred embodiment of a jig and bracket assembly, embodying principles of the present invention, remote from a tooth to which the bracket is to be secured.

Referring to FIGS. 1–4, a representative tooth 10 of a patient is illustrated. The representative tooth 10, in the figures, is arbitrarily chosen for purposes of illustration as a lower right second bicuspid on which an orthodontic bracket 20 is to be placed to form part of an orthodontic appliance with which the teeth of the patient are to be treated. Usually, an orthodontic appliance is formed of a pair of archwires, one upper and one lower, and archwire supporting brackets, twenty to twenty-eight in number, one mounted to each of the upper and lower teeth. Typically, slotted brackets are used on the teeth mesial of the molars, while often in lieu of slotted brackets, four or eight buccal tubes, sometimes secured by bands, are mounted to each of the first and/or second molars, to support the distal end of the respective upper or lower archwire.

The bracket 20, illustrated in the drawings, is representative of any of the brackets of the appliance. Such a bracket 20 includes a supporting base or pad 22 to which is fixed an archwire support 23. Although sometimes, as with buccal tubes particularly, the base 22 is welded to a crown encircling band which is set around the tooth, in the illustrated embodiment, the bracket 20 is designed for mounting to the tooth by direct adhesion of the pad 22 to the surface of the tooth crown by the application of a bonding cement. The support 23 typically includes a pair of horizontally spaced vertical wings 24 carrying upper and lower hooks 25 to which an archwire ligature is tied to secure an archwire to the bracket 20. Formed horizontally across the approximate centers of the wings 24 is a rectangular slot 27 into which an archwire of rectangular cross-section is to be supported and ligated to the bracket 20.

Figure 4:
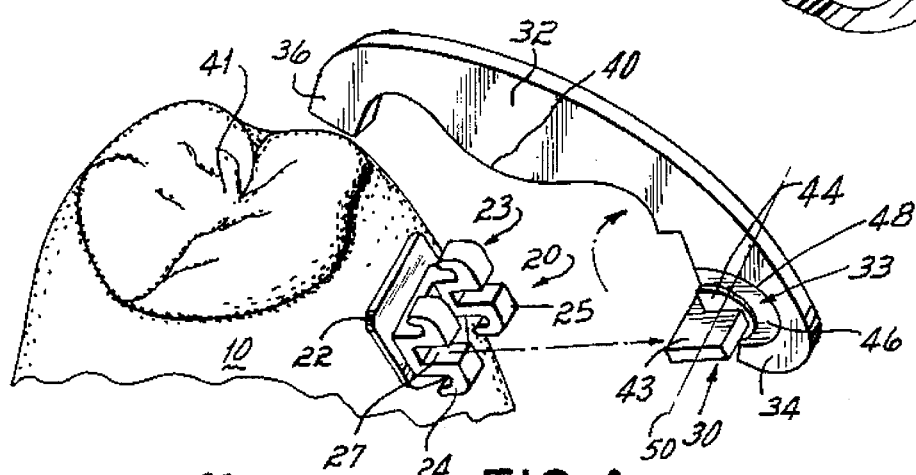
FIG. 4 is an isometric view similar to FIG. 3 illustrating the bracket placed on and secured to the tooth with the jig removed from the bracket.

It is a general objective in the design of standardized orthodontic appliances, and a particular objective in the design of customized orthodontic appliances, for the bracket 20 to support an archwire in the slot 27 at a specific position and orientation relative to the surface of the tooth 10. To achieve this objective, the slot 27 in the bracket support 23 is positioned and oriented relative to the pad 22 at a specific distance from, and angle relative to, the surface of the tooth on which the bracket is attached. This bracket geometry is effective to avoid or at least minimize the amount of archwire bending that is required by the orthodontist when the bracket is accurately positioned and oriented on the patient's tooth. The bracket geometry is effective for this purpose, however, only if the bracket is in fact accurately positioned and oriented on the tooth at the position and orientation for which it was designed. FIG. 4 illustrates an example of a bracket 20 so positioned and oriented on a tooth 10 in accordance with its intended design.

Figure 2:
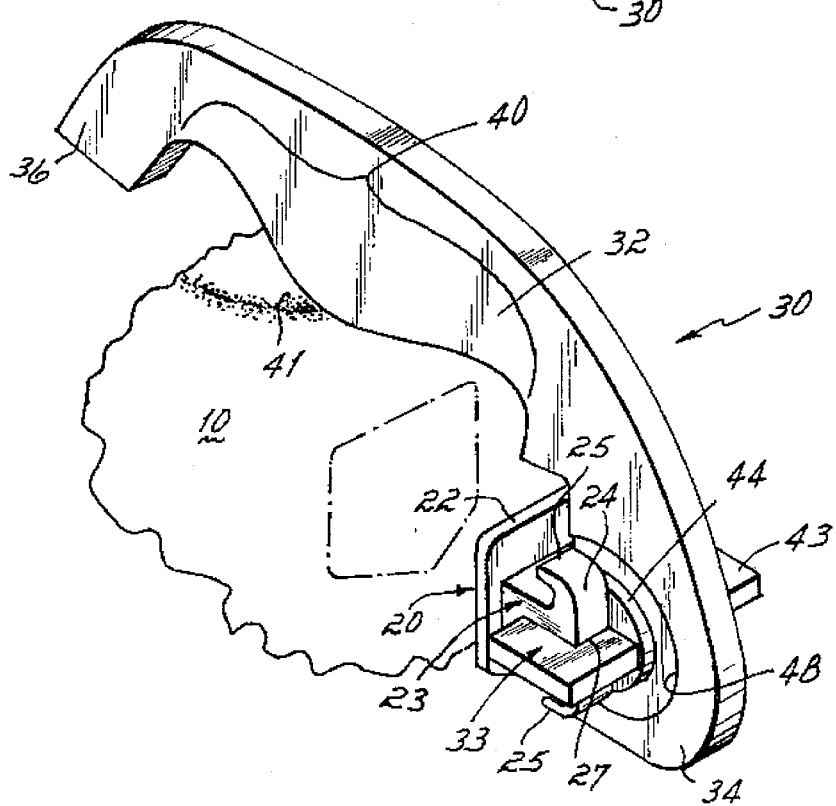
FIG. 2 is an isometric illustration of the assembly of the orthodontic bracket placement jig of FIG. 1 with the orthodontic bracket positioned for placement of the jig on a tooth.
Figure 3:
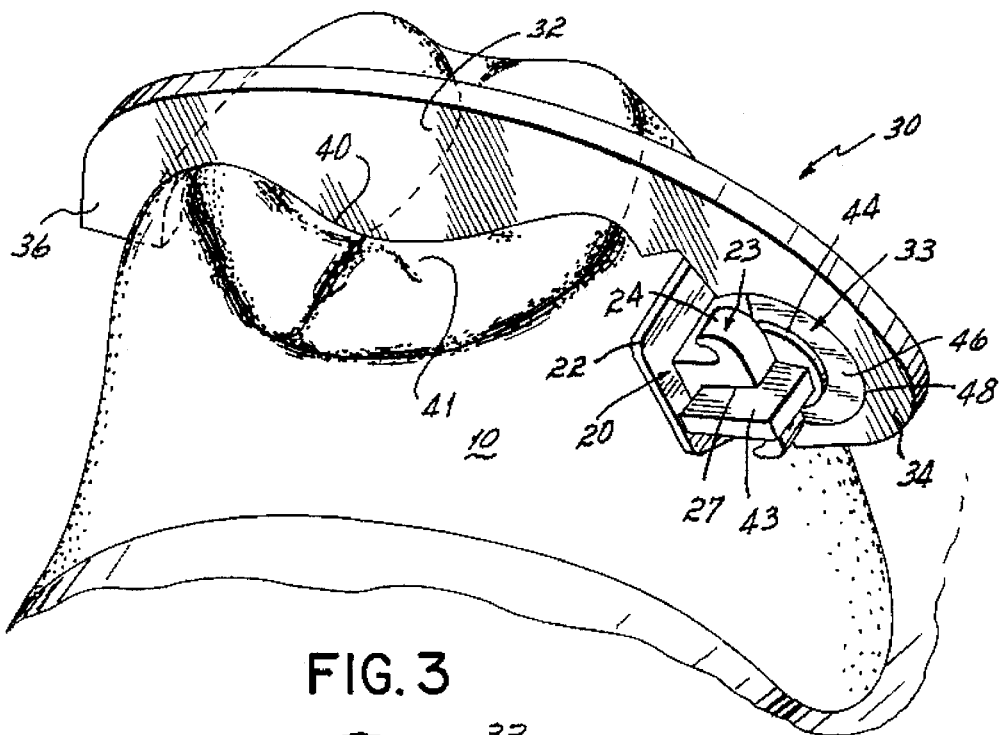
FIG. 3 is a perspective view of the jig assembly of FIGS. 1 and 2 illustrating a tooth with an orthodontic bracket positioned thereon in accordance with the present invention.

FIG. 2 illustrates the orthodontic bracket 20 assembled with a bracket placement jig 30 according to one embodiment of the present invention. This preferred embodiment of the jig 30 is formed of two parts. One part is a tooth-engaging part 32 and the other part is a axial part that may, in some embodiments, be in the form of a bracket-supporting part 33. These parts 32 and 33 are more clearly illustrated in the disassembled view of FIG. 1. The tooth-engaging part 32 of the jig 30 has a pivot end 34, a free end 36 opposite the pivot end 34, and a tooth-engaging surface 40 therebetween, which, in this embodiment, is two-dimensional, conforming in shape to the contour 41 of the surface of the tooth 10 in a vertical labial-lingual plane, when the jig 30 is positioned over the tooth 10 as illustrated in FIG. 3.

The bracket-supporting part 33 of the jig 30 includes a registration surface configured to releasably engage the bracket 20 while maintaining the archwire slot 27 of the bracket 20 in a specific orientation and position relative to the point of connection between the jig parts 32 and 33. In one form, the registration surface in part includes a blade 43, which is configured to fit into the slot 27 of the bracket 20, a spacer 44 which fits between the wings 24 of the support 23 of the bracket 20 and is fixed to the blade 43 so as to hold the blade 43 at the same orientation and position relative to the spacer 44 as the slot 27 has relative to the wings 24 of the bracket 20. The blade 43, although more positively maintaining the angle of the slot, is optional, particularly with the three dimensional jig 60 of FIG. 6, which positions the bracket more precisely on the tooth such that the proper angle of the slot 27 will be achieved by the more accurate fitting of the jig to the tooth, and without the blade 43.

In the two-part jig 30, surrounding the spacer 44 is a circular convex inner bearing surface 46 having a groove 47 therein to pivotally support the pivot end 34 of the tooth-engaging part 32 of the jig 30. The pivot end 34 of the tooth-engaging part 32 of the jig 30 has formed therein a circular concave outer bearing surface 48 which snaps over the surface 46 of the bracket-supporting part 33 of the jig 30. In an alternative embodiment as is better illustrated in FIG. 5, however, a cylindrical bracket 20a having a barrel type slotted support 23a is shown. With such a bracket 20a, the support 23a itself forms and functions as the axial part of a one part jig 30a, and thereby performs the function of the bracket supporting part 33 of the jig 30 of FIGS. 1–4, above.

With either the two part jigs 30 or the one part jig 30a, the outer bearing surface 48 spans an arc of slightly more than 180°. Thus, with the two part bracket 20, the two parts 32 and 33 of the jig 30 will hold together but can be easily disconnected once the bracket 20 is secured to the tooth 10. With the one part jig 30a, the jig part 32 and the barrel 23a of the bracket 20a hold together and are easily disconnected once the bracket 20a is secured to the tooth 10. In addition, where the blade 43 is used, the blade 43 may be ligated to the bracket using a standard ligature which may be employed to tie the blade 43 in the bracket slot 27 in much the same way an archwire is tied.

Figure 5:
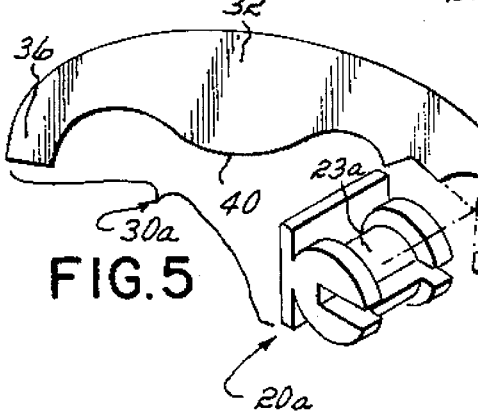
FIG. 5 is a side disassembled isometric view of an alternative embodiment of the jig of FIGS. 1–4 illustrating a one piece jig and cooperating bracket.

The bracket 20 is secured to the tooth 10 by starting with the assembly of the bracket 20 connected to the bracket-engaging part 33 of the jig 30 of FIGS. 1–4, or with the cylindrical bracket 20a of FIG. 5, to which is assembled the tooth engaging portion 32 of the jig 30 or 30a, as illustrated in FIG. 2. Then, if not previously applied, adhesive is applied to the pad 22 of the bracket 20 so that the bracket and jig assembly can be placed on the tooth 10, as illustrated in FIG. 3. This placement may be achieved with the orthodontist using the thumb and middle finger. When the assembly is approximately in position on the tooth 10, the orthodontist will press the tooth-engaging part 32 of the jig 30 toward the tooth 10, preferably using the index finger, so that the tooth-engaging surface 40 of the jig 30 firmly seats over the crown of the tooth in a precise and unique position and orientation, thereby locating and orienting the bracket 20 at its precise design connection point on the tooth 10. The placing action of the jig 30a, for example, onto the tooth 10 is facilitated, by pivoting the contour of the surface 40 about an axis 50 of the pivot point connection between the jig part 32 and bracket barrel 23a of the jig 30a, as illustrated in FIG. 5. A similar motion occurs in the placement of the two part embodiment of the jig 30 as it pivots about the axis of the pivot connection between the jig parts 32 and 33. The jig 30a used with the bracket 20a of FIG. 5, used with a blade 43, will not pivot at the interconnection of the tooth engaging part 32, but can effectively position the bracket 20a, particularly when used with the cap 62 of the jig 60 of FIG. 6, with its three-dimensional tooth engaging surface. Further, the jig 30a used without a blade 43a, as illustrated in FIG. 5, will more reliably assume its proper orientation on the tooth when used with a jig having the three dimensional properties illustrated in FIG. 6, described below.

Figure 6:
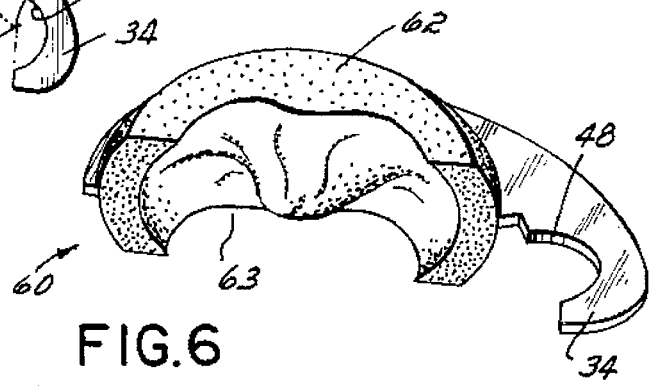
FIG. 6 is a perspective view of an alternative embodiment to the jig of FIGS. 1–5 having, instead of a two-dimensional tooth engaging surface, a three-dimensional tooth-engaging jig surface in the form of a cap that fits over the occlusal end of the tooth.

The jigs 30 and 30a described above use a two-dimensional surface 40 conforming to the profile of the tooth along a vertical plane through the bracket connection point on the tooth 10. However, a jig having a three dimensional tooth engaging surface such as the jig 60, illustrated in FIG. 6 is preferred, with the tooth-engaging surface being formed as a partial cap 62 that conforms in three-dimensions to a portion of the crown surface at the occlusal end of the tooth 10. Such a three-dimensional cap 62 has a three-dimensional internal recess 63 which, like the surface 40 of the two-dimensional version 30 of the jig, conforms to the tooth profile in vertical cross-section through the connection point of the bracket to the tooth 10. In addition, the three-dimensional surface of the recess 63 further conforms in a mesial-distal direction or elsewhere on the crown of the tooth to the three-dimensional surface of the tooth. The three-dimensional conformity to the surface of the crown preferably conforms to the entire occlusal tip of the tooth, to thereby more reliably position the bracket 10 at its proper position and orientation on the tooth 10. The cap 62 with the three-dimensionally contoured surface of the recess 63 facilitates the speed and ease of the use of the jig 30 in positioning the bracket on the tooth 10, and increases the precision with which the bracket can placed on the tooth 10.

While the above embodiments of the invention are described for brackets on the facial side of the teeth and for buccal tubes, the jigs of this invention are also useful for lingually mounted brackets and tubes.

From the description above, those skilled in the art will appreciate that various additions and modifications can be made to the jig, and method to connect brackets to teeth with the jig, without departing from the principles of the present invention.

Therefore, the following is claimed:

1. A jig for positioning an orthodontic bracket on the crown of a tooth of a patient wherein the crown has a shape that is characteristic of the that of a crown of a specific tooth of the patient, the jig comprising:

a tooth engaging part having a pivot end and a tooth-engaging surface thereon spaced from the pivot end, the surface conforming in shape to at least an extended portion of the shape of the crown, the extended portion including a contour conforming in at least two dimensions to the portion of the shape of the crown of the tooth; and an axial part having a pivot axis thereon pivotally connected to the pivot end of the tooth engaging part, the pivot axis being oriented in a horizontal mesial-distal direction when the tooth engaging surface is in intimate conforming engagement with the crown of the tooth;

the axial part having a bracket engaging surface thereon spaced from the pivot axis a distance equal to the distance from the pivot end of the tooth engaging part to the bracket when the tooth engaging surface is in intimate mating engagement with the crown of the tooth and the bracket is located at a unique position and orientation on a tooth.

2. The jig of claim 1 wherein:

the axial part is separate from the bracket and the bracket engaging surface includes external registration surface geometry conforming to internal surface geometry of an archwire slot of the bracket.

3. The jig of claim 2 wherein:

the registration surface geometry is in the form of a blade.

4. The jig of claim 1 wherein:

the tooth-engaging surface is a three-dimensional cap and the contour conforms in three dimensions to the portion of the shape of the crown of a tooth.

5. An orthodontic bracket and positioning jig assembly for positioning the orthodontic bracket on the crown of a tooth of a patient wherein the crown has a shape that is characteristic of the that of the crown of a specific tooth of the patient, the assembly comprising:

an orthodontic bracket having a base, an archwire support rigidly extending from the base and an archwire slot formed in the support;

a bracket positioning jig having a tooth engaging part and an axial part pivotally interconnected at a pivot axis, the bracket being releasably connected to the jig at the axial part;

the tooth engaging part having a tooth-engaging surface conforming in shape to at least an extended portion of the shape of the crown, the extended portion including a contour conforming in at least two dimensions to the portion of the shape of the crown of the tooth;

the axial part and tooth engaging part being dimensioned to extend from the bracket, when the bracket is mounted in a predetermined position and orientation on the facial side of the crown of the tooth, to the tooth-engaging surface of the tooth engaging part when the tooth-engaging surface is in intimate mating engagement with the crown of the tooth; and the pivot axis being horizontally oriented and spaced horizontally from the tooth when the tooth-engaging surface is in intimate mating engagement with the crown of the tooth.

6. The assembly of claim 5 wherein:

the tooth-engaging surface is a three-dimensional cap shaped to contact the crown of a tooth to uniquely position and orient the jig in three-dimensions on the crown.

7. The assembly of claim 5 wherein:

the archwire support includes a pair of mesial-distally spaced vertical tie wings rigidly extending from the base, the archwire slot including two coplanar portions, one formed in each of the wings; and the jig has a part thereof geometrically configured to snugly fit between the spaced tie wings to locate the bracket in a mesial-distal direction relative to the tooth engaging part.

8. A jig for positioning an orthodontic bracket on a tooth of a patient comprising:

a tooth engaging part having a pivot end and a tooth-engaging surface thereon spaced from the pivot end, the surface being configured to fit in a unique position and orientation on the occlusal extremity of the tooth, when moved gingivally thereagainst, to uniquely position and orient the tooth engaging part on the tooth;

an axial part pivotally connected to the end of the tooth engaging part at a pivot axis that is oriented in a mesial-distal direction when the tooth engaging part is uniquely positioned and located;

the jig having geometry configured to releasably engage an orthodontic bracket having an archwire slot therein so as to locate the bracket at a specific position and specific orientation relative to the pivot axis, and at a unique position and orientation on a tooth, when the tooth engaging part is uniquely positioned and located on the tooth; and the tooth-engaging surface is a two-dimensional contour of the tooth along a vertical labial-lingual plane approximately bisecting the crown of the tooth across the occlusal extremity thereof.

9. A jig for positioning an orthodontic bracket on a tooth of a patient comprising:

a tooth engaging part having a pivot end and a tooth-engaging surface thereon Spaced from the pivot end, the surface being configured to fit in a unique position and orientation on the occlusal extremity of the tooth, when moved gingivally thereagainst, to uniquely position and orient the tooth engaging part on the tooth;

an axial part pivotally connected to the end of the tooth engaging part at a pivot axis that is oriented in a mesial-distal direction when the tooth engaging part is uniquely positioned and located;

the jig having geometry configured to releasably engage an orthodontic bracket having an archwire slot therein so as to locate the bracket at a specific position and specific orientation relative to the pivot axis, and at a unique position and orientation on a tooth, when the tooth engaging part is uniquely positioned and located on the tooth; and the axial part is integral with an orthodontic bracket and has a cylindrical surface adapted for engagement by the pivot end of the tooth engaging part.

10. An orthodontic bracket and positioning jig assembly for positioning the orthodontic bracket on a tooth of a patient comprising:

an orthodontic bracket having a base securable at a predetermined location on the surface of a tooth of a patient, the bracket having an archwire support rigidly extending from the base and an archwire slot formed in the support and dimensioned, positioned and oriented to support an orthodontic archwire at a predetermined position and orientation on the tooth;

a bracket positioning jig having a tooth engaging part and an axial part pivotally interconnected at a pivot axis;

the tooth engaging part of the jig having a tooth-engaging surface configured to fit on the occlusal end of the tooth in a unique position and orientation;

the axial part and tooth engaging part being configured such that the jig supports the bracket in a predetermined position and orientation with respect to the tooth-engaging surface of the tooth engaging part when the tooth-engaging surface thereof is fit onto the tooth in the unique position and orientation;

the pivot axis being oriented such that the tooth-engaging surface moves to and from the unique position and orientation on the tooth by movement parallel to the base of the bracket supported by the jig; and the tooth-engaging surface is a two-dimensional contour of the occlusal end of the tooth in a vertical labial-lingual plane approximately bisecting the crown of the tooth.

11. An orthodontic bracket and positioning jig assembly for positioning the orthodontic bracket on a tooth of a patient comprising:

an orthodontic bracket having a base securable at a predetermined location on the surface of a tooth of a patient, the bracket having an archwire support rigidly extending from the base and an archwire slot formed in the support and dimensioned, positioned and oriented to support an orthodontic archwire at a predetermined position and orientation on the tooth;

a bracket positioning jig having a tooth engaging part and an axial part pivotally interconnected at a pivot axis;

the tooth engaging part of the jig having a tooth-engaging surface configured to fit on the occlusal end of the tooth in a unique position and orientation;

the axial part and tooth engaging part being configured such that the jig supports the bracket in a predetermined position and orientation with respect to the tooth-engaging surface of the tooth engaging part when the tooth-engaging surface thereof is fit onto the tooth in the unique position and orientation;

the pivot axis being oriented such that the tooth-engaging surface moves to and from the unique position and orientation on the tooth by movement parallel to the base of the bracket supported by the jig; and the tooth-engaging surface is shaped to partly surround the crown of the tooth and is positioned relative to the axis so as to pivot over and onto the crown of the tooth and uniquely position and orient the bracket on the surface of the tooth.

12. A method of positioning and orienting an orthodontic appliance for connection to the crown of a tooth of a patient, the method comprising the steps of:

providing an orthodontic appliance for connection to the crown of the a tooth of a patient;

providing a jig having a pivot axis and a tooth engaging surface conforming to the shape of the occlusal end of the crown of the tooth, the tooth engaging surface being in a fixed position and location relative to the pivot axis;

engaging the appliance at a predetermined position and orientation relative to a pivot axis;

positioning the jig adjacent the tooth of the patient, with the pivot axis oriented approximately mesial-distally, to locate the appliance proximate the crown of the tooth;

pivoting the jig about the axis to move the tooth engaging surface gingivally into engagement with the occlusal end of the crown of the tooth to thereby position and orient the appliance on the crown of the tooth;

fixedly securing the appliance to the crown of the tooth;

pivoting the jig to move the tooth engaging surface thereof occlusally and out of engagement with the crown of the tooth; and disengaging the appliance from the jig.

13. The method of claim 12 further comprising the step of:

providing a placement jig having an appliance-engaging member for engaging the appliance in the predetermined position and orientation, the member being pivotally connectable to the jig to pivot about the pivot axis.

14. The method of claim 12 further comprising the preliminary step of:

custom forming the tooth engaging surface of the jig to sufficiently conform to a portion of the surface of the crown of a tooth of an individual patient so that, when the jig is pivoted into engagement with the occlusal end of the crown, the tooth engaging surface will be uniquely positioned and oriented relative to the tooth.

* * * * *